(12) United States Patent
Feuilloley et al.

(10) Patent No.: US 6,984,360 B1
(45) Date of Patent: Jan. 10, 2006

(54) METHOD AND DEVICE FOR STERILIZING HOLLOW BODIES

(75) Inventors: Guy Feuilloley, Le Havre Cedex (FR); Véronique Bernard, Le Havre Cedex (FR)

(73) Assignee: Sidel S.A., LeHavre (FR)

( * ) Notice: Subject to any disclaimer, the term of this patent is extended or adjusted under 35 U.S.C. 154(b) by 0 days.

(21) Appl. No.: 09/622,359

(22) PCT Filed: Feb. 4, 1999

(86) PCT No.: PCT/FR99/00253

§ 371 (c)(1),
(2), (4) Date: Sep. 15, 2000

(87) PCT Pub. No.: WO99/40949

PCT Pub. Date: Aug. 19, 1999

(30) Foreign Application Priority Data

Feb. 16, 1998 (FR) .................................. 98 01937

(51) Int. Cl.
*A61L 2/20* (2006.01)

(52) U.S. Cl. .................. 422/28; 422/292; 422/298; 422/302; 422/304; 141/6; 21/56

(58) Field of Classification Search ................ 422/292, 422/298, 302, 304, 305, 307, 28; 141/6; 21/56

See application file for complete search history.

(56) References Cited

U.S. PATENT DOCUMENTS

| | | | | |
|---|---|---|---|---|
| 3,042,533 A | * | 7/1962 | McConnell et al. | .......... 422/34 |
| 3,795,483 A | * | 3/1974 | Grafingholt | .................. 422/37 |
| 4,992,247 A | * | 2/1991 | Foti | .......................... 422/304 |
| 5,031,673 A | * | 7/1991 | Clusserath | ...................... 141/6 |

FOREIGN PATENT DOCUMENTS

DE            43 05 478            8/1994

* cited by examiner

*Primary Examiner*—John Kim
*Assistant Examiner*—Brad Y. Chin
(74) *Attorney, Agent, or Firm*—Sughrue Mion, PLLC

(57) ABSTRACT

The invention concerns a method and a device for sterilising hollow bodies, such as containers, container preforms, tubes and various conduits. The invention is characterised in that it consists in guiding (15) a vaporisable sterilising agent over the walls of the hollow body (9), using guide means (7; 13) enabling the agent to be entirely deposited over the surfaces to be sterilised.

32 Claims, 2 Drawing Sheets

METHOD AND DEVICE FOR STERILIZING HOLLOW BODIES

The invention concerns a method for sterilizing hollow bodies. It is most particularly applied, although not exclusively, to sterilizing containers between their fabrication and their filling, or even sterilizing of preforms or blanks of containers at the time of the manufacturing process of sterile containers. It also concerns a device for implementing the method.

Sterilization in the sense of the present invention means any procedure that tends to destroy or reduce elements (microbes, germs, yeasts, etc.) which, if they develop, cause the contents of the hollow body to be inappropriate for the usage or consumption for which it is intended. This term does not necessarily mean a "zero" degree of contamination for one type of element or another, but an acceptable degree as a function of contents, of usage, of its desired shelf life or other parameters. Thus we speak of clean or sterile hollow bodies, depending on the degree of contamination remaining.

Numerous methods have been envisioned to obtain sterile hollow bodies. But they have not been satisfactory for various reasons.

Typically, the basic principle is to inject a sterilizing fluid into the hollow bodies, or on the exterior if there is a need for not only the interior but also the exterior to be sterile.

It is this fluid that is used and the operating method applied which determines the degree of sterilizing achieved.

Known processes consist in immersing the hollow bodies or in filling them with a sterilizing liquid. These methods require draining, then drying of the hollow bodies, on one hand; they involve a great consumption of fluid, on one hand, or even require recycling of significant volumes of the sterilizing liquid, on the other.

Draining, as well as drying, when the body has been completely filled, are delicate operations; it is important that these operations not become the cause of new contamination.

On the other hand, the recycling of the liquid, if consumption reduction is desired, requires a complex installation. Other methods consist in the use of sterilizing gases. The installations for this application are complex and have a high consumption. Thus, for example, there have been conceptions of manufacturing the sterile containers of plastic materials, such as bottles, by insufflating them with sterile air or air with the addition of sterilizing agents. Obtaining sterile air is an operation that requires methods that become more massive, the greater the volume necessary for insulation. In fact, it should be remembered that to manufacture bottles of plastic material by using the injection-insulation technique, insulation pressures are on the order of 40 bars, which means that the fabrication of a one-liter bottle involves the use of 40 liters of air. In addition, after insulation, it is necessary to de-gas the containers. Depending on the nature of the sterilizing agent used, it may be impossible to conceive of releasing it into the atmosphere, which again entails the necessity of a complex recycling installation.

Methods have thus been conceived which consist of atomizing a liquid sterilizing agent (such as hydrogen peroxide, peracetic acid or other) and applying it in the form of droplets on the surfaces to be sterilized of the packaging material.

The methods of this type and the corresponding devices known to date are not fitting in that they do not make it possible to ensure a distribution of the sterilizing agent over all of the internal surface, also called the interior wall, of the hollow body when it is essentially this surface which must be sterilized; in addition, the known devices are not "universal" in the sense that they do not make possible the processing of hollow bodies having shapes that are different from each other or even that they are not suitable for processing of every type of material.

Thus, for example, the device described in U.S. Pat. No. 4,631,173 does not make it possible to ensure a homogeneous distribution of the agent since it uses a heated surface on which the sterilizing agent is projected with force. In contact with this surface, the agent vaporizes, on one hand, and is sent toward the surfaces to be sterilized. It is necessary to aim the heated surface so that the agent can be dispersed in the hollow body.

Thus, it is necessary to adapt the configuration and the orientation of the heated surface to the volume and to the shape of the hollow bodies. If the hollow body is very deep, it is not certain that the sterilizing agent will be sent toward the surfaces that are furthest away.

This device is not appropriate for sterilizing bottles or preforms (or blanks) of bottles since their opening is not large enough so that the dispersed product may be directed to the interior of this type of hollow body except if it has a heating surface of very small dimensions so that it can be introduced into the opening of the container. But in this case, it would be difficult to bring the sterilizing agent in contact even with this surface. In addition, the heat energy necessary for vaporizing would be likely to deteriorate the hollow body (bottle or preform) when it is made of a thermosensitive material.

The procedure described in the German patent request 43 05 478 does not make it possible to ensure homogeneous distribution of the sterilizing agent and is not appropriate for every type of material making up the hollow bodies.

It does not make it possible to ensure homogeneous distribution of the sterilizing agent since the latter is injected by means of a nozzle which opens out toward the base of the hollow body. The agent is introduced into the nozzle in a mixture with water vapor in order to, in theory, go into the vapor phase in the hollow body. However, if the tube cools, the water vapor-sterilizing agent condenses, and then the drops fall to the base of the body instead of the vapor mist. Because of this, there is a risk of accumulation of drops on the base and not an ascent of the agent on the walls.

In order to reduce the risk of accumulation and/or prevent condensation of the agent at the bottom of the container, it is provided that the hollow bodies will be reheated, which makes it possible to reactivate the vaporizing of the agent.

This does not in any way ensure that the vaporized agent will distribute itself properly over all the walls of the hollow body.

In addition, this reheating method makes this operation impossible with certain types of materials, particularly thermosensitive materials (plastics) or insulating materials. In fact, a hollow body of thermosensitive material has the risk of being deteriorated by the method (risk of deformation by retraction of the material in particular); an insulating material considerably increases the processing temperature since the supply of heat by reheating the hollow body is carried out on the exterior; at the limit, it will become impossible to implement the method as the necessary heating time becomes greater.

This method again makes it necessary to modify, in particular, the installation (change in the reheating chamber) in the case of changing the shapes or the sizes of the hollow bodies to be sterilized.

Another disadvantage of this method is that a lack or an absence of sterilizing agent in case of failure of a control system will not be detected since the agent is normally mixed with water vapor. In the case of injection of water vapor alone, the absence of a sterilizing agent cannot be easily detected by an external observer.

Other approaches have been taken which consist in particular of propelling the sterilizing agent in the hollow body using a compressed gas.

This solution does not make possible the assurance of a proper distribution of the agent since at the time of its introduction under pressure it creates compression knots and nodes, turbulent phenomena, or other obstacles to the said distribution.

Thus, the object of the invention is a method and a device that does not present one or the other of the disadvantages mentioned above, i.e. which makes possible: a distribution over all of the surface of the sterilizing agent; a possibility of application without significant modification of the device in the case where the hollow bodies to be sterilized are changed; an application to all types of hollow bodies (bottles, pots, flasks, troughs, tubes, etc.); an application to any type of material; easy detection of an absence of sterilizing agent.

According to the invention, a method for sterilizing hollow bodies, particularly of containers or preforms of containers, by prior application of a sterilizing agent on the surfaces to be sterilized, is characterized in that it consists of causing a gaseous current that moves the vaporized agent toward all of the surfaces to be sterilized in order to distribute it on all of the said surfaces.

Thus, by moving, i.e., by guiding, the agent onto the surfaces, a proper distribution is obtained, in contrast to the devices where the agent is projected or insufflated into the interior. A simple guiding of the agent after it has been vaporized makes the procedure useful with any type of material since, in particular, there is no need to heat the hollow bodies; as will be explained below, the method may be used with a relatively simple device that can be used for any type of hollow bodies no matter what their shape or dimension and without there being a need to modify them, in particular in shape and/or dimensions of the bodies; finally, the absence of agent is easily detectable; it is adequate simply to confirm the arrival of the agent at the moment of vaporizing.

Another advantage is that the guiding of the agent by a gaseous guiding current makes it possible to carry out the sterilizing no matter what the position of the hollow bodies, i.e. no matter what the position of their openings (top, bottom or other).

According to another characteristic, the agent is vaporized on the outside of the hollow bodies close to its opening, and the guiding current is implemented by causing an aspiration of the vaporized sterilizing agent using an aspirating means acting opposite the opening of the hollow body.

According to another characteristic, in an installation for implementation intended for sterilizing tubes that are open at their two ends, the aspiration is caused using a device acting across from the end of the tube opposite to that in the area of which the vaporizing is carried out.

According to another characteristic of the method according to the invention, the phases of vaporizing and introduction of the agent into the hollow body are preceded by a phase of withdrawing particles or non-adhering elements that are present in the hollow body, such as dust introduced during storage.

According to another characteristic, the vaporizing phase is followed, after a period of contact, by a phase of withdrawal (drying) of the remaining sterilizing agent.

Other characteristics and advantages of the invention will become apparent from reading the description that follows given with regard to the figures attached, in which:

Figure 1:
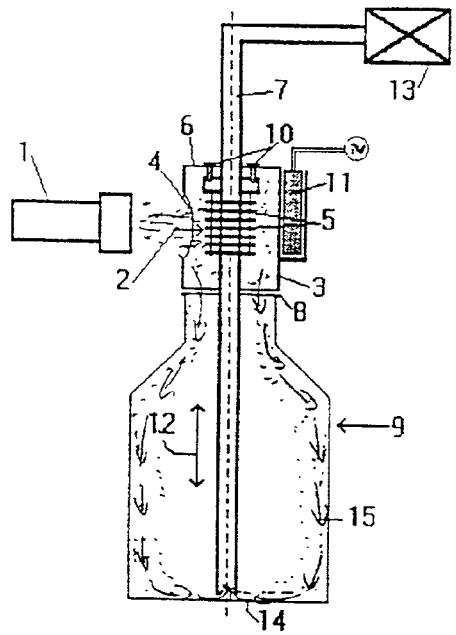
FIG. 1 is a schematic diagram of a device for sterilizing hollow bodies conforming to the invention.

The device shown in FIG. 1 comprises an injector or atomizer 1 for the sterilizing agent that can be vaporized such as hydrogen peroxide, peracetic acid or any other suitable agent. The injector is connected on one hand to a reservoir for the agent, not shown, and to control means for its opening and closing on the other hand.

The injector may be mechanical, electromechanical, pneumatic or from any other appropriate type.

The output of the sterilizing liquid from the injector is directed toward an evaporator 2 enclosed in housing 3, cylindrical in the example illustrated. An opening 4 is arranged in the cylindrical wall of the housing across from the injector output in order to permit atomizing of the liquid on the evaporator 2.

In the embodiment shown, the evaporator 2 is made up of a cylinder of a material that is a good thermal conductor and provided on its periphery with blades 5 in the form of annular protuberances. Preferably, the blades are distributed evenly over the height of the cylinder making up the evaporator body.

The external diameter of the evaporator is less than the interior diameter of the housing 3 so that after evaporation, the sterilizing agent may circulate, as will be explained below.

Housing 3 is closed, on its upper end in the picture, by a cover 6 with an opening at its center for the passage of a hollow tube 7.

Preferably, as shown in the figure, the tube 7 passes across an axial orifice, not referenced, of evaporator 2.

The lower end of the housing is intended to be located across from the opening 8 of the hollow body 9 (in this case a container such as a bottle) to be sterilized. It is open and, preferably, the shape and the interior dimensions of the opening of the end correspond to that of the interior opening of the hollow body.

The evaporator 2 is held in place in the housing 3 using fastening means 10 such as screws or spacer sleeves arranged close to the end of the evaporator that is furthest away from the hollow body 9 in order not to interfere with the trajectory of the agent between the evaporator 2 and the hollow body 9.

The reheating means 11 of the evaporator 2 are provided to bring it to a temperature that makes possible semi-instantaneous evaporation of the sterilizing agent when it arrives in contact. In the example shown, these means 11 are made up of a heating resistor arranged in the thickness of the wall of the housing 3 in such a way as to reheat the latter and to reheat the evaporator 2 by thermal conduction across the material that makes up housing 3 and evaporator 2 and/or by confection in the free space between the interior wall of the housing 3 and evaporator 2.

Preferably, at least the tube 7 can be slid (double arrow 12) to facilitate placement of the hollow body with respect to the device. Thus, the hollow body 9 may be placed across from the device by simple lateral translation by moving the tube away from the trajectory of the hollow body. It is thus possible to use transfer systems known in and of themselves to ensure the placement of the hollow bodies such as transfer gripper mechanisms mounted on articulated arms or even transfer mechanisms with wheels or plates having notches or sockets for guiding the hollow bodies.

Alternatively, it could be conceived that the placement of the hollow body is carried out by subjecting it to an axial translation, tube 7 remaining fixed.

In one embodiment, only the tube 7 slides. Thus, it slides relative to the hollow body and the assembly made up by the evaporator 2 and the housing 3 at the time of the placement or withdrawal of the hollow body.

In one variation, it is the tube 7 and the assembly consisting of evaporator 2, housing 3 which are translated axially at the time of placement or withdrawal of the hollow body 9.

The end of the tube 7 located on the side of the cover 6 of housing 3 is connected to an aspiration source 13. When the hollow body 9 is in place, as is shown in FIG. 1, the end of the tube opening out into the hollow body 9 is close to the base 14 of it.

The device function is as follows.

Evaporator 2 is heated by heating means 11 in such a way that its temperature would be adequate to cause immediate evaporation of the sterilizing agent when the latter projected by the injector 1 arrives at its contact.

By way of example, when the agent is hydrogen peroxide, the evaporator 2 is brought to a temperature between 100° C. and 400° C., preferably on the order of 150 to 200° C.

The opening 8 of the hollow body 9 is placed across from the opening of the housing without ever coming into contact with it so that an air current can be created between the orifice 4 of the housing 3 and the gap that exists between the container and the housing.

In addition, the fact that a distance is maintained between the housing and the hollow body prevents deterioration of the latter when it is made of a thermosensitive material.

Tests have given evidence that a distance between 0.1 mm and 5 mm will obtain good results and that the best results would be obtained by allowing a distance between 0.5 and 3 mm to exist.

Preferably, the device is maintained in a sterile air environment in a housing to prevent additional dust particles from penetrating into the hollow bodies to be sterilized. For this, known means are used such as an isolation chamber with laminar sterile air flow in which the device is installed.

After the device and the hollow body 9 have been placed in the correct position relative to each other, the sterilizing agent is atomized or injected by the injector or atomizer 1 on the evaporator 2 across the orifice 4 arranged in the housing 3. The high temperature of the evaporator 2 causes immediate vaporizing of the sterilizing agent and the aspiration promoted by means 13 across the tube 7 opening near the base 14 of the hollow body 9 creates a guiding current in the air contained in the hollow body along with a guiding of the vapors of the sterilizing agent, which are thus directed to the interior of the hollow body 9 and are deposited on the internal surface of the hollow body. This current is indicated schematically by arrows 15 on the figure.

In addition, given that the hollow body is at ambient temperature, the sterilizing agent condenses when contacting the internal surface of the hollow body.

After a specified period of contact, the sterilizing agent contained in the hollow body is withdrawn.

Tests carried out on preforms of containers of plastic material (PET) or on the containers themselves show that a period of contact between 2 and 6 seconds makes it possible to obtain a degree of asepsis compatible with standards for foodstuffs in force, by using hydrogen peroxide concentrated to 35% as the sterilizing agent.

Aspiration across tube 7 may be continuous or sequential. If it is sequential, it is important that it starts at the latest at the moment of injection in order that all of the sterilizing agent injected and vaporized will be aspirated toward the hollow body. One consequence of aspiration starting with a slight delay from the injection would be the risk of loss of a certain quantity of agent by evaporation toward the outside, notably by way of orifice 4. This risk of loss does not exist any longer if the aspiration starts at the moment of injection.

In addition, whenever it is sequential, it must be continued at least until all of the surface to be treated is covered with sterilizing agent.

At the end of the contact period mentioned above, the hollow body is sterile. However, it is necessary to withdraw the sterilizing agent, for example by drying the hollow body if the agent is liquid.

In order to do this, it is possible to insufflate a sterile gas such as dry or hot sterile air in the hollow body, i.e. preferably to drive the hot air to the inside of the hollow body by aspiration. In fact, insulation with hot air is difficult in the case of hollow bodies having a specific geometry, for example in the case of bottles where the flow of air is preferentially directed toward the bottom but does not come in contact with all of the walls.

Figure 2:
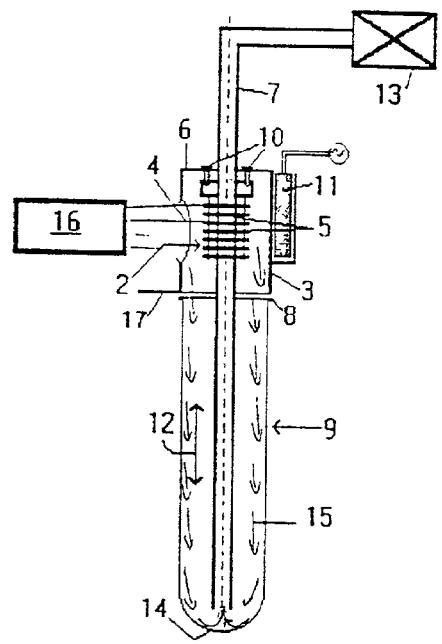
FIG. 2 is a schematic diagram of a device for withdrawing the sterilizing agent after a determined contact time.

In addition, an advantage of the solution consisting of guiding hot air is that it is possible to use the same device as that employed for vaporizing and deposit of sterilizing agent by substituting for injector 1 a heat generator 16 such as is shown in FIG. 2.

In the case of the use of hot air, the heat generator 16 may be a hot air nozzle at high temperature or a burner. The heat or the flame is directed toward the orifice 4 and simultaneously an aspiration is created in the hollow body (in this case, a preform of a container) to channel the flame due to the heat toward the walls.

Use of a flame or of a hot air generator is not contraindicated for drying hollow bodies of thermosensitive material such as containers or preforms of containers of thermoplastic material.

In fact, the time of exposure to the heat is very short. Taking into account the thermal inertia of the material, the guided hot air simply has the function of sweeping or drying the hollow body.

Still, when the hollow body to be sterilized is of thermoplastic material, it is preferable to provide means for preventing a direct transfer between the output of the generator 16 and the exterior of the hollow body 9.

These means may be made up by a plate 17 for protection of the opening of the hollow body encircling at least partially the housing 3 and arranged between the orifice 4 of the hot air passage of the flame and the opening of the housing 3 on the side of the hollow body 9, as is visible in FIG. 2.

Alternatively, a hood could be provided that largely covers the opening of the hollow body.

Figure 3:
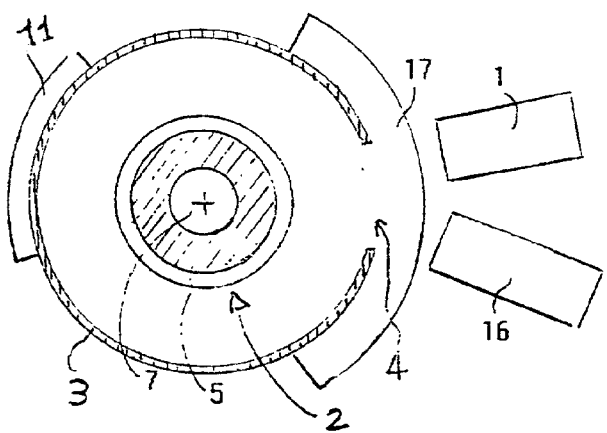
FIG. 3 is a schematic view from above of a variation of a device according to the invention.

In FIG. 3, there is a schematic illustration in cross section view from above at the level of the orifice 4, of a possible arrangement of a single device serving simultaneously for depositing the sterilizing agent and for drying.

Simultaneously, the outputs of an injector 1 and that of a hot air generator 16 are directed toward the orifice 4 of the housing 3. In this case, it is necessary that the generator 16 of hot air be of the sequential type so that the heat (flame or hot air) will not be applied during the injection/vaporizing/contact of the sterilizing agent phases.

Preferably, the drying phase for the hollow body is carried out in two steps: a first step in which heat (flame or hot air) is applied in the housing, the aspiration being active; and a second in which the aspiration continues while the heat is no longer applied in such a way that all of the vapor residues will be evacuated.

By way of example, it would be possible to dry the preforms of containers of thermoplastic material by applying a flame for 1 to 3 seconds at the orifice 4 and by continuing aspiration between 2 and 6 seconds.

Figure 4:
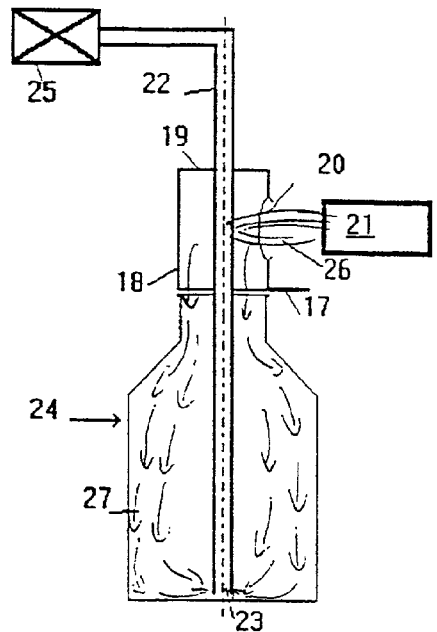
FIG. 4 is a schematic view of a device used for withdrawal of the sterilizing agent.

FIG. 4 represents a schematic cross section of a device provided specifically for drying the hollow bodies.

The main difference from the device in FIGS. 1 to 3 is that it no longer includes the evaporator.

It comprises a housing 18 in the form of a cylindrical tube 19 closed at one of the ends and open at the other. The housing has an orifice 20 across from which a heat generator 21 is located, a burner for example.

A cross rod 22 crosses the housing in such a way that one 23 of its ends is located close to the base of the hollow body 24. The other end of the rod is connected to an aspiration device 25.

When the heat, in this case a flame 26, is applied at the same time as the aspiration, a flow is created (arrows 27) aspirating the flame and the vapors of the sterilizing agent and drying the interior surface of the hollow body.

Preferably, the phase of injection/vaporizing of the agent is preceded by a phase of withdrawing, from the hollow body, of particles such as dust or other elements that do not adhere.

This phase may be carried out by aspiration and/or insulation or any other appropriate method.

In one embodiment, a device similar to that used for withdrawing traces of the sterilizing agent and shown in FIG. 4 is used with the difference that the device does not contain a hot air generator. Thus, the device comprises the means of aspiration 22, 23, 25 and a housing 18.

In a variation, instead of aspiration by the rod 22, the phase of withdrawal prior to the injection of the agent is no longer carried out by aspirating using the rod 22, but by aspirating using the housing 18 by way, for example, of the orifice 20. In this case, the rod 22 makes it possible to supply the air compensating the vacuum created at the time of aspiration.

In one embodiment, all of the phases mentioned above are carried out with one and the same device, such as the one shown in FIG. 3, and thus comprising an evaporator, means of aspiration, means of injecting the agent and a hot air generator, i.e., all of the means shown in more detail in FIGS. 1, 2 and 4.

However, for reasons of efficiency of the various processes to be carried out, it is advantageous to implement at least the preliminary phase of dust removal in a separate device from the one or the ones used for the later phases of sterilizing, i.e., injection/vaporizing/contact and drying.

In fact, the first phase consists of recovering the dust or other particles while in the time afterward, this includes the gas or vapors that are aspirated. The dust or other particles must be recovered and disposed of while the gas or vapors of sterilizing agent may be recycled. Thus, if it is desirable to arrange gas vapor recycling, it is necessary to have separate means of aspiration and it is desirable to differentiate the respective devices.

In addition, the use of a single device is not suitable when the device must have higher rates of speed, for example, when the hollow bodies to be sterilized are preforms of containers (bottles or others) of plastic material brought in succession, in line, to the intake of a machine for blow molding containers or containers at the end of fabrication.

In such a case, it is desirable and preferable to separate all of the phases and to implement them by moving the hollow bodies along a line to the separate phases, making in-line processing possible.

Figure 5:
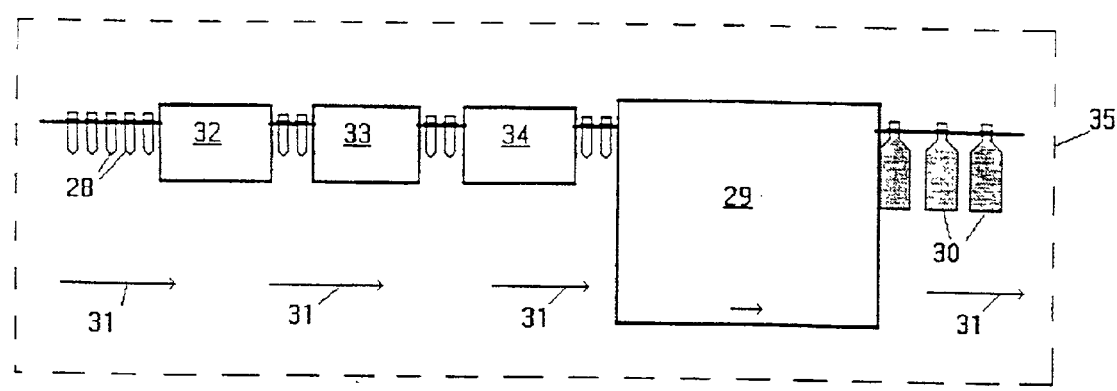
FIG. 5 is a block diagram of an installation using the invention.

FIG. 5 illustrates the schematic diagram of an installation that makes it possible to carry out all of the phases mentioned above at the time of processing preforms 28 for sterilizing them upstream of a machine 29 of blow molding/filling of containers 30.

The preforms 28, arriving continuously in line in the direction of arrows 31, are successively brought into a stage 32 of withdrawal (dust removal or other). This step comprises the means, not shown, for processing several preforms.

Then, the preforms are transferred to a step 33 carried out by injection, vaporizing and contact of a sterilizing agent. This step comprises one or more devices conforming to those in FIG. 1.

Then the preforms are transferred to a step 34 of drying. It should be noted that the time of transfer between the preceding state and the latter state can be well used for prolonging the time of contact necessary for sterilizing.

Then, the preforms are transferred to the machine 29 for fabrication/filling of the containers.

Preferably, the machine 29 and the various steps of processing 32, 33, 34 are enclosed in a sterile enclosure with laminar flow.

This enclosure is shown schematically by the broken line 35 in FIG. 5.

Each of these processing steps, 32, 33, 34 respectively, may comprise at least one appropriate fixed device to which the hollow bodies are brought step by step for their processing.

However, this structure is not well adapted to high rates of processing speed required in a number of installations; it is for this reason that preferably each step is carried out in order to permit in-line processing of the hollow bodies.

In one embodiment, each step comprises the means to hold or support the hollow body associated with the means for continuous transport. It is thus possible to process the hollow bodies gradually as they arrive in the installation. The rate of processing is a function of the dimensions of each of the stages and thus of the number of devices that each includes.

The rate of processing is a function of the size of each of the stages and thus of the number of devices incorporated in each.

In one variation that is not shown, the sterilizing phases are carried out after fabrication of the containers, for example, before they are filled. Various steps, notably that 33 for sterilizing itself, are then downstream of the output of machine 29. In this case, machine 29 must not be in the laminar flow of sterile air; but it is important that at least the steps 33, 34 of sterilizing and drying would themselves be under laminar flow.

Figure 6:
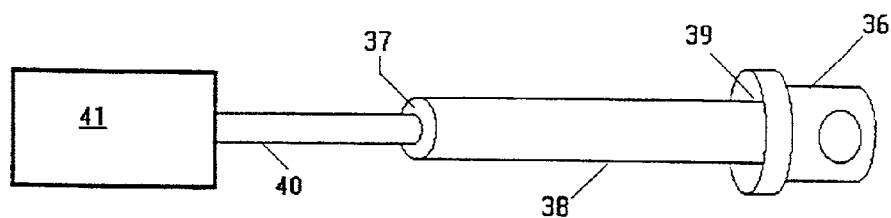
FIG. 6 is a diagram of a variation of the devices in FIGS. 1 to 4.

FIG. 6 shows a schematic diagram of the invention when it is used for sterilization of hollow bodies that are open at two of their ends. This is the case, e.g. with tubes or various conduits.

In this case, the aspiration is not carried using a tube crossing the housing 36 and opening out at the end 37 of the hollow body 38 opposite to the one 39 close to which the housing 36 is located with the injection means (not shown) and/or the means for generating hot air (not shown); rather, it is implemented using a tube 40 located at the open end 37 of the hollow body opposite the one 39 where the housing is located. The tube 40 is connected to aspirating means 41.

Naturally, the invention is not limited only to the embodiments described. It encompasses all the possible equivalent and varied embodiments.

What is claimed is:

1. A method for sterilizing a hollow body (9) having an opening (8) by depositing on a surface of the hollow body to be sterilized a sterilizing agent that is previously vaporized, comprising:

vaporizing the agent outside of the opening of the hollow body; and distributing the vaporized agent on the surface to be sterilized by creating a gaseous current for guiding the vaporized agent toward the surface to be sterilized by use of a means of aspiration, which has an opening that is within the hollow body and opposite the opening of the hollow body.

2. A method for sterilizing a hollow body (38) having two openings by depositing on a surface of the hollow body to be sterilized a sterilizing agent that is previously vaporized, comprising:

vaporizing the agent outside of one of the openings of the hollow body; and distributing the vaporized agent on the surface to be sterilized by creating a gaseous current for guiding the vaporized agent toward the surface to be sterilized by use of a means of aspiration, which has an opening that is within the hollow body and opposite the opening outside of which the agent is vaporized.

3. The method according to claim 1, wherein the sterilizing agent is an agent in liquid phase.

4. The method according to claim 1, further comprising suppressing particles or non-adherent elements present in the hollow body prior to vaporizing and distributing the agent into the hollow body.

5. The method according to claim 4, wherein the suppressing of particles or non-adherent elements is carried out by insulation.

6. The method according to claim 4, wherein the suppressing of particules or non-adherent elements is carried out by aspiration.

7. The method according to claim 1, further comprising withdrawing the remaining sterilizing agent after vaporizing and after a period of contact by the agent with the surface to be sterilized.

8. The method according to claim 7, wherein withdrawing the remaining sterilizing agent is carried out by introduction of a withdrawal agent in the inside of the hollow body.

9. The method according to claim 8, wherein the withdrawal agent is a sterile dry or hot gas.

10. The method according to claim 9, wherein the withdrawal agent is brought by aspiration into the inside of the hollow body, by using aspiration means acting in the hollow body opposite its opening.

11. The method according to claim 8, wherein the withdrawal agent is hot air injected using a hot air nozzle.

12. The method according to claim 7, wherein withdrawing the remaining sterilizing agent is carried out with the use of a flame injected by a burner and brought by aspiration into the inside of the hollow body, by using aspiration means acting in the hollow body opposite its opening.

13. The method according to claim 8, wherein the withdrawal agent, is injected on the outside of the opening of the hollow body before being introduced into the inside of the hollow body.

14. A device for carrying out the method according to claim 1, comprising a means (1) for injection of a vaporizable sterilizing agent, an evaporator (2) disposed across from the output of the injection means (1), and a means of aspiration (7, 13; 40, 41), which has an opening within the hollow body, the means of aspiration acting inside the hollow body to cause a gaseous current to guide the vaporized agent toward the interior surfaces of the hollow body when the hollow body is in place with respect to the device.

15. The device according to claim 14, wherein the evaporator is enclosed in a housing (3; 36) arranged on the outside of the opening of the hollow body (9; 38) and provided with an opening (4) across from the output of the means (1) of injection, and wherein the housing has an open end having a shape and interior dimensions corresponding to those of the opening of the hollow body (9; 38).

16. The device according to claim 14, wherein the means of aspiration (7, 13; 40, 41) comprise a tube (7; 40) connected to an aspiration source (13; 41).

17. The device according to claim 16, wherein the hollow body is in the shape of a container, such that it is open at one of its ends and closed at the other, and wherein the tube (7) is disposed through the opening of the hollow body, and the tube has a first end located at the base of the hollow body and a second end located at a side of a housing (3), the second end being connected to the aspiration source (13).

18. The device according to claim 17, wherein the tube (7) crosses the evaporator (2) and the housing (3).

19. The device according to claim 16, wherein the hollow body (38) is a tube or a conduit open at two opposite ends, and wherein the aspiration is carried out by arranging the aspiration tube (40) at the end of the hollow body opposite the end where the injection of the vaporizable sterilizing agent takes place.

20. The device according to claim 14, comprising means for withdrawing the sterilizing agent after a period of contact in the hollow body.

21. The device according to claim 20, wherein the means for withdrawing comprise a generator (16; 21) for dry or hot sterile air.

22. The device according to claim 21, wherein the generator is a burner (21).

23. The device according to claim 21, wherein the generator (16;21) is placed outside of the opening of the hollow body, and the generator has means to direct heat inside the hollow body.

24. The device according to claim 23, wherein the means to direct the heat comprises an aspiration tube (7; 22; 40) having an aspiration end with an opening in the hollow body in a zone such that heat is directed into all of the hollow body.

25. The device according to claim 24, wherein the hollow body is a container, and the tube (7; 22) penetrates through the opening of the container and contains an opening at the base of the container.

26. The device according to claim 24, wherein the hollow body is a tube or a conduit, and the tube (40) is arranged at the end of the hollow body opposite to the end at which the heat generator (16; 21) is located.

27. The device according to claim 14, further comprising means for suppressing dust or other particles prior to vaporizing and distributing the sterilizing agent.

28. The device according to claim 27, wherein suppressing is carried out by aspiration and/or insulation.

29. The device according to claim 14, wherein the device is surrounded by a laminar flow (35) of sterile gas, in excess pressure.

30. An installation for manufacturing and/or filling containers, comprising a machine (29) for fabrication/filling of the containers and a device according to claim 14.

31. The method according to claim 3, wherein the sterilizing agent is hydrogen peroxide or peracetic acid.

32. The device according to claim 29, wherein the sterile gas is air.

* * * * *